Figure 1:
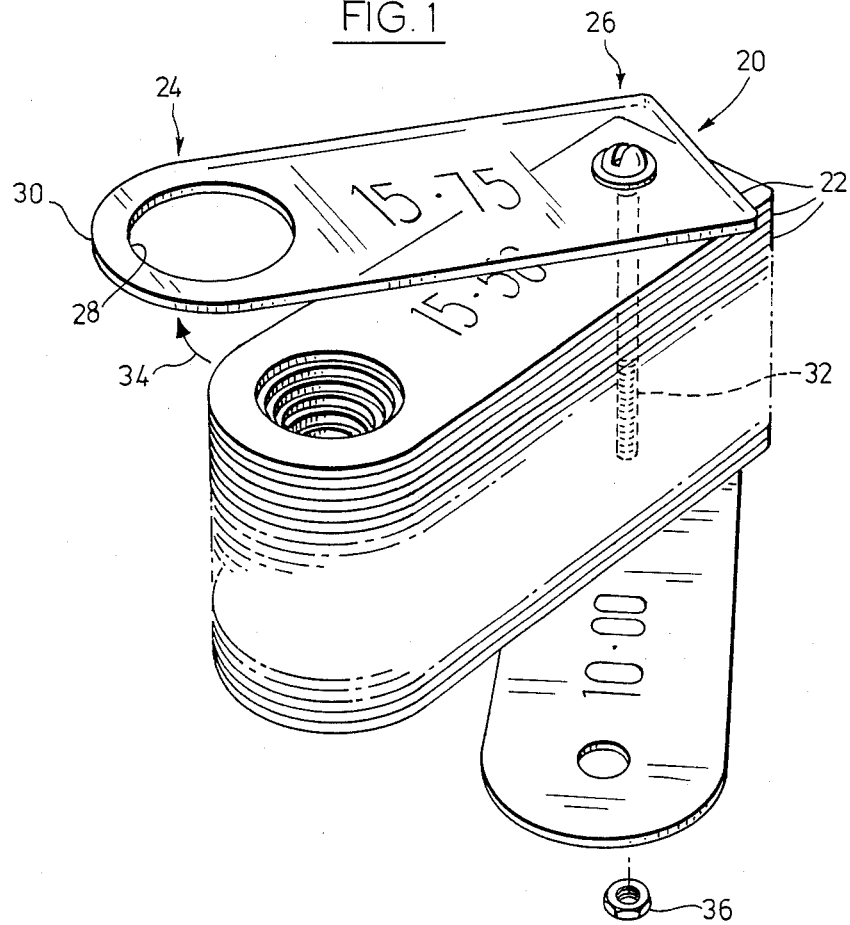

United States Patent [19]

Morin

[11] Patent Number: 4,517,747
[45] Date of Patent: May 21, 1985

[54] CORNEAL TEMPLATE SET
[75] Inventor: J. Donald Morin, Toronto, Canada
[73] Assignee: The Hospital For Sick Children, Toronto, Canada
[21] Appl. No.: 506,748
[22] Filed: Jun. 22, 1983
[51] Int. Cl.³ ............................ G01B 3/34; A61B 3/00
[52] U.S. Cl. .................................... 33/178 B; 33/512; 351/205; 351/247
[58] Field of Search ............ 33/174 D, 174 A, 178 B, 33/200; 351/200, 205, 219, 222, 247

[56]  References Cited
U.S. PATENT DOCUMENTS

| 867,011 | 9/1907 | Bromley | 33/178 B |
|---|---|---|---|
| 1,667,802 | 5/1928 | Homan, Jr. | 33/178 B |
| 1,755,152 | 4/1930 | Parker | 33/178 B |
| 3,993,045 | 11/1976 | Ion | 33/178 B |
| 4,160,330 | 7/1979 | Grolman | 33/200 |
| 4,211,241 | 7/1980 | Kaster et al. | 33/178 B |
| 4,309,085 | 1/1982 | Morrison | 351/219 |

FOREIGN PATENT DOCUMENTS

| 43468 | 12/1930 | Denmark | 33/178 B |
|---|---|---|---|
| 1351705 | 12/1963 | France | 33/178 B |

Primary Examiner—Richard R. Stearns
Attorney, Agent, or Firm—Rogers, Bereskin & Parr

[57] ABSTRACT

A template set for use in corneal size measurement. The templates take the form of identical thin and flexible blades rounded at one end, and are arranged in a stack in parallel planes. The blades are pivotally coupled together adjacent their opposite ends by a pivot pin which extends through the whole stack. The pivot pin allows individual blades to be pivoted out of the stack for use. Each blade has a circular opening adjacent the rounded end of the blade and the openings are graduated in size in predetermined increments from one end of the stack to the other. Each blade is also visibly marked to indicate the size of the opening.

6 Claims, 2 Drawing Figures

U.S. Patent   May 21, 1985   4,517,747

CORNEAL TEMPLATE SET

This invention relates generally to the field of ophthalmology and is concerned with particularly with a device for use in measuring the size of the cornea of the eye. Measurement of corneal size is necessary, for example, when a patient is to be fitted with contact lenses.

Traditional techniques for measuring corneal size involve the use of a linear rule or caliper held in front of the eye. The ophthalmologist or technician estimates the diameter of the cornea by visual comparison with the rule or caliper. It will be appreciated that these techniques are somewhat inconvenient to perform and may even be potentially dangerous to the patient; often, the rule or caliper will not be sterilized so there is a risk of infection if the rule of caliper touches the eye. Also, accuracy of measurement may be quite low because the ophthalomologist is attempting to estimate the overall size of a generally circular area using a linear measuring device.

An object of the present invention is to provide an improved device for use in corneal size measurement.

The device provided by the invention comprises a set of individual templates each in the form of a relatively thin and flexible blade of sterilizable material. Each blade has first and second ends and is formed with a circular opening which extends through the blade adjacent the first end. That end of the blade is rounded as seen in elevation and smooth so as to present a substantially non-injurious surface to the cornea in use. The blades are of substantially identical overall size and external shape and are arranged in a stack in which the blades are disposed in parallel planes with their respective second ends superimposed and coupled together by a common pivot pin which extends through the stack while allowing individual pivotal movement of each blade about said pin with respect to the other blades. The openings in the respective blades are graduated in size in predetermined increments from one end of the stack to the other and each blade is visibly marked to incidate the size of the opening in that blade.

The corneal template set provided by the invention has numerous practical advantages compared with the prior art discussed above. A primary advantage is convenience in use. The ophthamologist selects a template which he estimates may be of approximately the appropriate size and pivots that template out of the stack. Holding the remaining templates, the device is manipulated to bring the selected template directely in front of the cornea with the plane of the blade generally parallel to the front of the patient's face. The ophthamologist can then directly look through the opening in the end of the template at the cornea and make a direct comparison between the generally circular corneal area and the circular opening in the selected blade. If that opening is not of the correct size, the blade can be quickly pivoted back into the stack and the next size selected and tried. When the correct template has been identified, the corneal size can be read directly from the visible marking on the blade and that blade can be left projecting from the stack if required, for checking purposes later.

Preferably, the blades are made of a flexible plastic material and the device as a whole is sterilizable.

Figure 2:
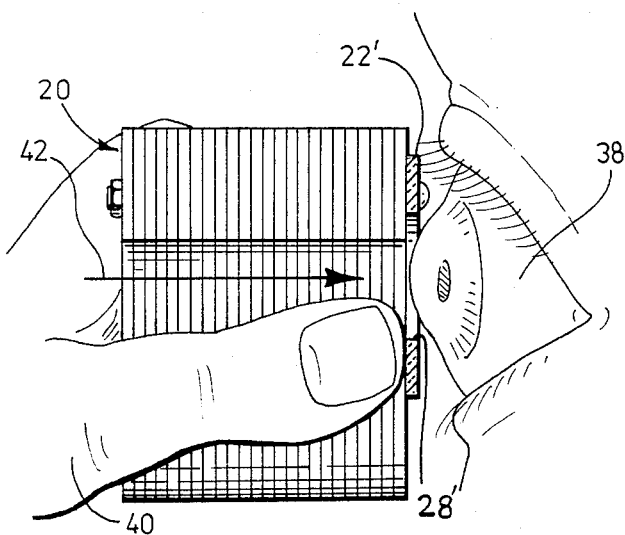

In order that the invention may be more clearly understood, reference will now be made to the accompanying drawings which illustrate a preferred embodiment of the invention by way of example, and in which:

FIG. 1 is a perspective view of a corneal template set in accordance with the invention; and, FIG. 2 is a side view of a patient's eye showing the set in use.

Referring first to FIG. 1, the device is generally indicated by reference numeral 20 and comprises a set of templates individually denoted by reference numeral 22. Each template takes the form of a relatively thin and flexible elongate blade of a sterilizable material. In this particular embodiment, the blades are cut from plastic sheet; the particular material is not believed to be critical but in this case the material used was a polycarbonate of the type sold under the trademark LEXAN.

Referring to the blade which appears at the top in FIG. 1 by way of example, each blade has first and second ends denoted respectively 24 and 26 and is formed with a circular opening 28 adjacent the first end. That end is rounded as seen in elevation (30) and smooth so as to present a substantially non-injurious surface to a patient's cornea. The blades are all of substantially identical overall size and external shape and are arranged in a stack in which the blades are disposed in parallel planes with their respective second ends superimposed and coupled together by a common pivot pin 32. The pin extends through the stack while allowing individual pivotal movement of each blade about the pin with respect to the other blades as indicated by arrow 34. In this particular embodiment, the pivot pin 32 takes the form of a bolt which extends through clearance holes in the blade and which is fitted with a nut 36 at its lower end as drawn.

The openings in the blades (as opening 28) are all circular in shape and are graduated in size in predetermined increments from one end of the stack of blades to the other. In addition, each blade is visibly marked to indicate the size of the opening in that blade.

In this particular embodiment, there are in fact 25 blades and the openings are graduated in size in increments of 0.25 mm, from the bottom blade in the stack as drawn, which has a diameter of 10 mm, to the top blade in the stack, which has a diameter of 15.75 mm. These sizes have been found in practice to provide the ophthamologist with a reasonable range of the normal corneal sizes encountered in practice. Thus, this particular form of the device is believed to be eminently suitable for dealing with the majority of corneal sizes likely to be encountered. Also, the increments (0.25 mm.) correspond with normal incremental sizes for contact lenses. However, other sizes and incremental differences between adjacent blades can of course be provided for special situations.

As indicated previously, the blades 22 are all of substantially identical shape except for the openings 28 and are all made of a thin and flexible plastic material. In this case, each blade is approximately 5 cm. long, 1.9 cm. wide and 1.5 mm. in thickness. The end of each blade is rounded approximately on a 1 cm. radius. For the larger sizes of template opening the end of the blade is radiussed about the center of the opening. This gives an approximate distance of 4–5 mm. between the periphery of the opening and the end of the blade. For smaller sizes, the center of the opening is displaced nearer to the end of the table so that the spacing between the periphery of the opening and the end of the blade is in the range 2–4 mm.

It is believed that, for easier manipulation of the device in practice, the spacing of the opening from the end of the blade is important and, specifically, should be in the range 2-5 mm.

FIG. 2 shows the template set 20 in use in practice. The eye of a patient is shown at 38 and the template set 20 is shown being held in front of the eye. One of the templates, denoted 22' has been pivoted out of the stack of templates and the remainder of the stack is being held by the ophthamologist, whose hand is indiated at 40. Template 22' is being held substantially parallel to the face of the patient with the opening 28' in the template directly in front of the cornea. The ophthamologist can then look directly through the opening in the direction of arrow 42 to make a direct comparison between the size of the opening and the size of the corneal area.

As indicated previously, the ophthamologist can readily change to a different template by pivoting the selected template back into the stack and pivoting out a different template until the correct size is determined. At that time, he or she simply reads the size of the opening from the face of the template; additionally, the template can remain in a position projecting from the stack for verification purposes.

It will of course be understood that the preceding description relates to a particular preferred embodiment of the invention only and that certain modifications are possible within the broad scope of the invention. For example, while the particular materials and dimensions referred are believed to be appropriate for providing a corneal template set which can be used in a wide variety of situations normally encountered by the practicing ophthamologist, other dimensions and materials can of course be used. The number of templates, the range of sizes of openings in the templates and the incremental size variation between the openings may vary. For example, in another embodiment fourteen templates may be used having openings in the range of 6 mm. to 12.5 mm. diameter at increments of 0.5 mm. Also, the outer end of each template need not of course be rounded in an arc.

I claim:

1. A device for use in corneal size measurement comprising:
   a set of individual templates each in the form of a relatively thin and flexible blade of transparent, sterilizable plastic material, the blade having first and second ends and being formed with a sharply defined circular opening extending through the blade adjacent said first end thereof, the blade being rounded in elevation and smooth at said first end so as to present a substantially non-injurious surface to the cornea in use;
   said blades being of substantially identical overall size and external shape and being arranged in a stack in which the blades are disposed in parallel planes with their respective second ends superimposed and coupled together by a common pivot pin which extends through the stack while allowing individual pivotal movement of each blade about said pin with respect to the other blades;
   the openings in the respective blades being of graduated size in predetermined increments from one end of the stack to the other and each blade being visibly marked to indicate the size of the opening in that blade.

2. A device as claimed in claim 1, wherein said said set comprises at least 25 blades.

3. A device as claimed in claim 1, wherein said openings are graduated in increments of 0.25 mm. in a range of from 10 to 15.75 mm. diameter.

4. A device as claimed in claim 1, wherein each blade has an overall length of 5 cm., a width of 1.9 cm. and has a radius of 1 cm. at its said outer end.

5. A device as claimed in claim 1, wherein said openings are spaced from the respective first ends of the blades by a distance in the range 2-5 mm.

6. A device for use in corneal size measurement comprising:
   a set of at least 25 individual templates each in the form of a relatively thin and flexible elongate plastic blade having first and second ends and being formed with a circular opening extending through the blade adjacent said first end thereof, the blade being rounded in elevation and smooth at said first end so as to present a substantially non-injurious surface to the cornea in use;
   said blades being of substantially identical overall size and external shape and being arranged in a stack in which the blades are disposed in parallel planes with their respective second ends superimposed and coupled together by a pivot pin which extends through the stack while allowing individual pivotal movement of each blade about said pin with respect to the other blades;
   the openings in the respective blades being of graduated size in increments of 0.25 mm. from one end of the stack of the other commencing with a minimum size of 10 mm. diameter, and each blade being visibly marked to indicate the size of the opening in that blade.

* * * * *